US005718681A

United States Patent [19]

Manning

[11] Patent Number: 5,718,681

[45] Date of Patent: Feb. 17, 1998

[54] MEDICATION DELIVERY STRAW

[75] Inventor: Christopher E. Manning, 7480 Champagne Pl., Boca Raton, Fla. 33433

[73] Assignees: Christopher E. Manning; David L. Krasnow, both of Coconut Creek, Fla.

[21] Appl. No.: 584,312

[22] Filed: Jan. 11, 1996

[51] Int. Cl.$^{6}$ .................... A61M 31/00

[52] U.S. Cl. .................... 604/56; 604/85; 239/33

[58] Field of Search .................... 604/48, 82, 83–85, 604/73, 77, 78–79, 57–58, 49, 56; 239/33; 210/263–264, 266; 141/343

[56] References Cited

U.S. PATENT DOCUMENTS

| | | |
|---|---|---|
| 214,617 | 4/1879 | Brown . |
| 1,000,332 | 8/1911 | Dyer . |
| 1,661,400 | 3/1928 | Yehle . |
| 2,302,591 | 11/1942 | Ahern . |
| 2,436,505 | 2/1948 | Du Rall . |
| 3,409,224 | 11/1968 | Harp et al. . |
| 3,463,361 | 8/1969 | Cook et al. . |
| 3,610,483 | 10/1971 | Visconti . |
| 3,826,409 | 7/1974 | Chlicoate . |
| 4,237,884 | 12/1980 | Erickson et al. . |
| 4,581,013 | 4/1986 | Allen . |
| 4,998,623 | 3/1991 | Doull . |
| 5,085,335 | 2/1992 | Carbaugh . |
| 5,119,560 | 6/1992 | Noble . |
| 5,156,335 | 10/1992 | Smith et al. . |
| 5,181,505 | 1/1993 | Lew et al. . |
| 5,203,459 | 4/1993 | Wade . |
| 5,222,940 | 6/1993 | Wilk . |
| 5,282,789 | 2/1994 | Lundy . |
| 5,440,976 | 8/1995 | Giuliano et al. . |
| 5,509,605 | 4/1996 | Cripe . |

*Primary Examiner*—Mark Bockelman
*Assistant Examiner*—Ellen Tao
*Attorney, Agent, or Firm*—John C. Smith

[57] ABSTRACT

A medication delivery straw which delivers medication held within the straw tube. When the patient drinks fluid through the straw, the medication is dissolved and ingested by the patient. A particle barrier at one end of the straw prevents viscous or powdered medicines, or crushed tablets, from falling out of the straw. The particle barrier has apertures which allow fluid to enter the straw during use. The fluid dissolves the medication in the straw while the patient is drinking. Optional features include disposable funnels (which may be preloaded with medicine) for filling the straw with the correct dosage of medication, funnels which are capable of attaching to pill crushers, removable caps for straws with premeasured doses of medication that prevent medicine loss during handling or storage, flexible necks for ease of use, and flexible straw walls to allow crushing medicine tablets within the straw. In the alternative, a medicine sack holds the medication much like a teabag holds tea. The medicine sack is secured inside the fluid path of the straw and fluid passes through the walls of the medicine sack to dissolve the medication. Other embodiments use preloaded straws which may contain either crushable tablets or breakable cartridges.

24 Claims, 14 Drawing Sheets

MEDICATION DELIVERY STRAW

BACKGROUND OF THE INVENTION

1. Technical Field

The present invention relates to medication delivery devices. In particular, it relates to devices useful for delivering oral does of medication to patients.

2. Background Art

Historically, a significant portion of a nurse's time is consumed by the process of administering medication to patients. For relatively able patients, all that may be required is the delivery of a pill and a glass of water. However, even for this simple task, the time required to administer medication to an entire hospital ward is significant.

While liquid medications can be difficult to administer, dry medications present special problems. This is due to the fact that dry medication must be mixed with another medium prior to administering it. This injects additional time delays, questions related to the accuracy of dosage, and increased costs.

A larger problem is associated with patients who are not able to quickly take their medication. For example, small children, elderly or senile patients, mentally handicapped patients and severely injured patients may require more time to administer medication because of their inability to follow instructions or to physically take medication. As a result, delivery of medication to this category of patients is difficult and time consuming.

Past attempts to orally administer medication to this category of patients has centered on mixing the medication with other types of edible items. For example, pills or powdered medications are often crushed and mixed with food, such as apple sauce. Several problems are associated with this type of medication delivery. First of course is that this approach is very time consuming. Further, since the medicine is mixed with food items, the patient must eat all of the food to ensure proper dosage. In the case of handicapped patients, even when the nurse hand feeds the patient, food may be spilled from the patients mouth resulting in loss of medication. Likewise, the patient may decide not to eat any more food, in which case the nurse must then attempt to convince a confused or senile patient that the meal is not over. Due to the excessive amounts of time and the uncertainty of dosage amounts, this historic approach to medication delivery has been found wanting.

Another approach has been to design special purpose utensils designed to allow the nurse to administer medication orally. While this approach can reduce the amount of time required to administer medication, it has the drawback of requiring expensive special purpose utensils which are usually disposable. In addition, dry medication is usually mixed with a liquid in the utensil which requires extra time to prepare and care on the part of the nurse.

The prior art has failed to provide a dry medication delivery device which ensures proper dosage, is easy to use, and allows to the nurse to complete medication rounds in a more timely fashion and is inexpensive.

SUMMARY OF THE INVENTION

The present invention solves the foregoing problems by providing a medication delivery straw which contains dry medication within the straw tube. When the patient drinks fluid through the straw, the medication is dissolved and ingested by the patient. In one embodiment, a particle barrier at one end of the straw prevents powdered or medicines or crushed tablets from falling out of the straw. The particle barrier has apertures which allows fluid to enter the straw during use. The fluid dissolves the medication in the straw while the patient is drinking. Optional features include funnels for filling the straw with the correct dosage of medication, preloaded funnels which act as sealed containers for medicine prior to use, removable caps for straws with premeasured doses of medication and that prevent medicine loss during handling or storage, flexible necks, and flexible straw walls to allow crushing medicine tablets within the straw. An alternative embodiment uses a medicine sack to hold the medication. The medicine sack is secured inside the straw in the path of the fluid which passes through the walls of the medicine sack and dissolves the medication. Other embodiments use capped straws which may contain crushable tablets or breakable cartridges to store medicine inside the straw prior to use. Alternative funnel embodiments include funnels which attach to tablet crushers and preloaded funnels which act as sealed medicine containers prior to use.

DESCRIPTION OF THE PREFERRED EMBODIMENT

Prior to a detailed discussion of the drawings, a general discussion of the features and advantages of the invention follows. The medication delivery straw (hereinafter: straw) provided herein allows a nurse to quickly and inexpensively administer dry medications to patients who would otherwise have difficulty ingesting all or part of the medication. The straw has a particle barrier at one end which allows fluid to pass through but retains the medicine in the straw prior to use. When the patient drinks fluids (for example, fruit juice) through the straw, fluid enters the straw and dissolves the medicine. By crushing tablets into small pieces, they are small enough to dissolve in the straw and be swallowed with the liquid.

In the preferred design, the straw is disposable. An optional flexible neck is provided to allow the patient more comfortable drinking positions. Likewise, an optional disposable funnel is provided to allow easier loading of the straw. Alternative embodiments include straw which come preloaded with medication and are capped to seal the medication in the straw until use.

An advantage to the straw is that it ensures that the entire dosage is ingested. In prior art methods, such as mixing medicine with food, it is possible that portions of the medicine will not be swallowed. The straw provides more consistent dosage control. Another advantage of the straw is that it allows the nurse to save time by reducing the amount of time required to administer the medication. An advantage to the patient is that it is easier and more comfortable to take the medicine than by prior art methods.

Figure 1A:
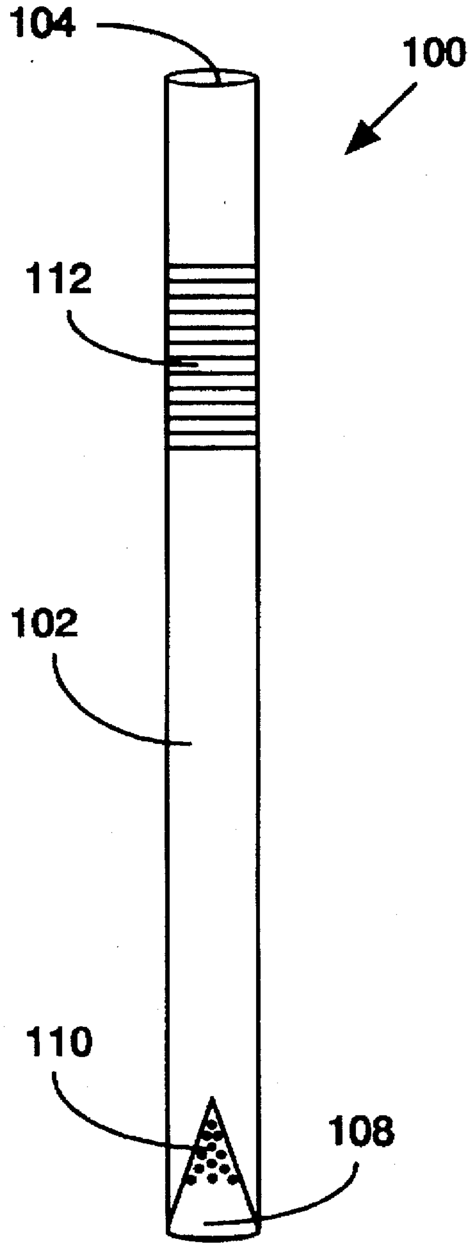
FIG. 1A illustrates a preferred embodiment of the medication delivery straw.
Figure 1B:
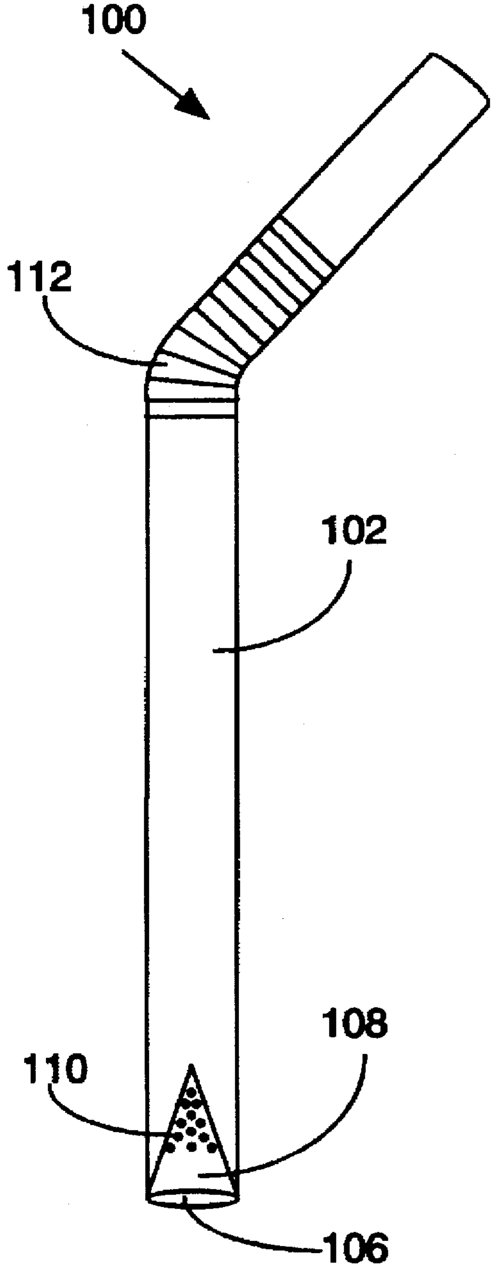
FIG. 1B shows the embodiment of FIG. 1A with the flexible neck bent during use.

Referring to FIGS. 1A and 1B, these figures illustrate a preferred embodiment of straw 100. Fluid tube 102 is shaped like an ordinary drinking straw. The preferred embodiment uses a length of approximately 7.5 inches with a 0.25 inch interior diameter. The preferred construction material is plastic. However, the dimensions and materials used are not critical so long as the patient can comfortably drink from straw 100. Optional flexible neck 112 (as shown in FIG. 1B) allows straw 100 to bend for the patients comfort. Proximal aperture 104, at the proximal end of fluid tube 102 is the end of the straw 100 from which the patient drinks. At the distal end 106 of fluid tube 102 is particle barrier 108. Particle barrier 108 includes barrier apertures 110 which allow fluid to be sucked into straw 100 by the patient.

In the embodiment of FIGS. 1A–B, barrier apertures 110 are 0.025 mm in diameter. However, the diameter size of barrier apertures 110 is not critical and may vary. The only requirement is that they must be small enough to retain substantially all of a dry medicine dose, such as a crushed tablet, in fluid tube 102. The location of the barrier apertures 110 can vary. However, in the preferred embodiment, a small number of barrier apertures (typically 10–12) are arranged around the upper two thirds of particle barrier 108.

In the preferred embodiment, particle barrier 108 is located at the tip of fluid tube 102 for ease of manufacture. However, particle barrier 108 can be located at any convenient point in the fluid path of fluid tube 102.

Figure 2A:
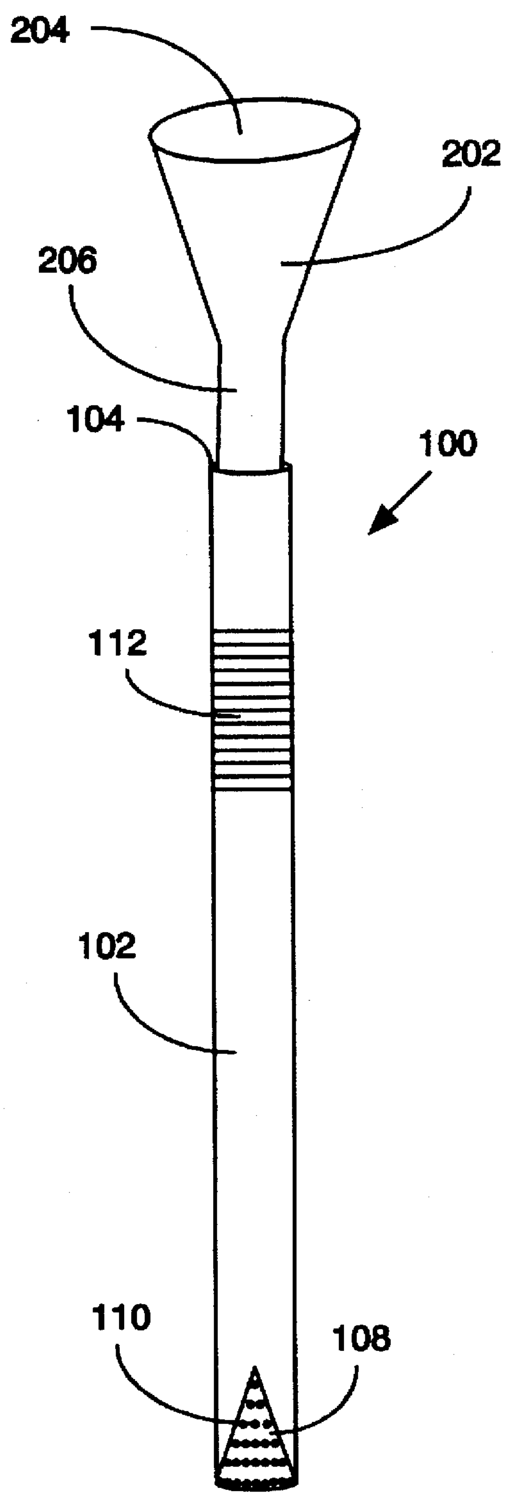
FIG. 2A shows the medication delivery straw with the optional funnel used to fill the medication delivery straw.

In FIG. 2A, optional funnel 202 is shown inserted into the proximal end of straw 100. The spout 206 is designed with an outside diameter suitable for insertion into the inside of fluid tube 102. Once spout 206 is inserted into fluid tube 102, powdered medicine or crushed tablets can be inserted into the funnel opening 204 of funnel 202. After the medication is loaded into fluid tube 102 via funnel 202, the nurse removes and discards funnel 202. The preferred embodiment envisions funnel 100 as being disposable. However, those skilled in the art will recognize that funnel 202 can be reusable.

Also shown in FIG. 2A is an alternative arrangement for barrier apertures 110. In this figure, barrier apertures 110 are not restricted to the upper portion of particle barrier 108. A disadvantage of this embodiment is that if very fine particles of medication result from the crushing process, they will tend to fall to the bottom of straw 100. In the earlier embodiment which located the barrier apertures 110 in the upper portion of particle barrier 108, there is less of a chance that any medication will be inadvertently lost.

Figure 2B:
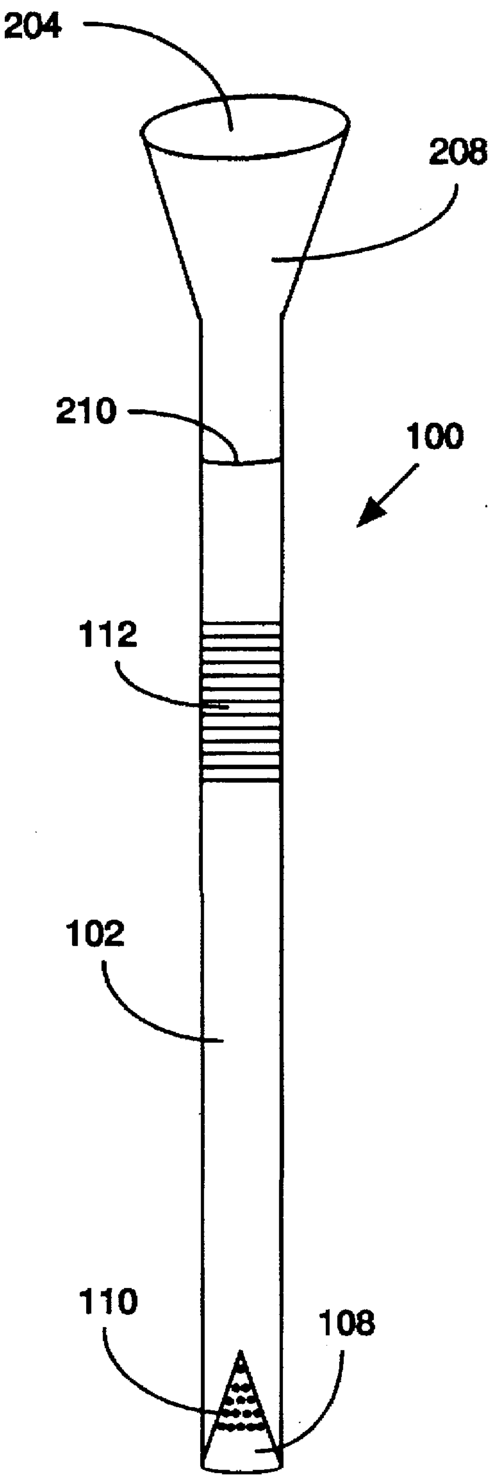
FIG. 2B shows an alternative embodiment of the medication delivery straw with an integral removable funnel.

In FIG. 2B, and alternative integral funnel 208 is shown. In this embodiment, integral funnel 208 is an integral part of straw 100. After the medication has been loaded into straw 100 by the nurse, integral funnel 208 is detached from straw 100 by tearing along weakened point 210.

Figure 3:
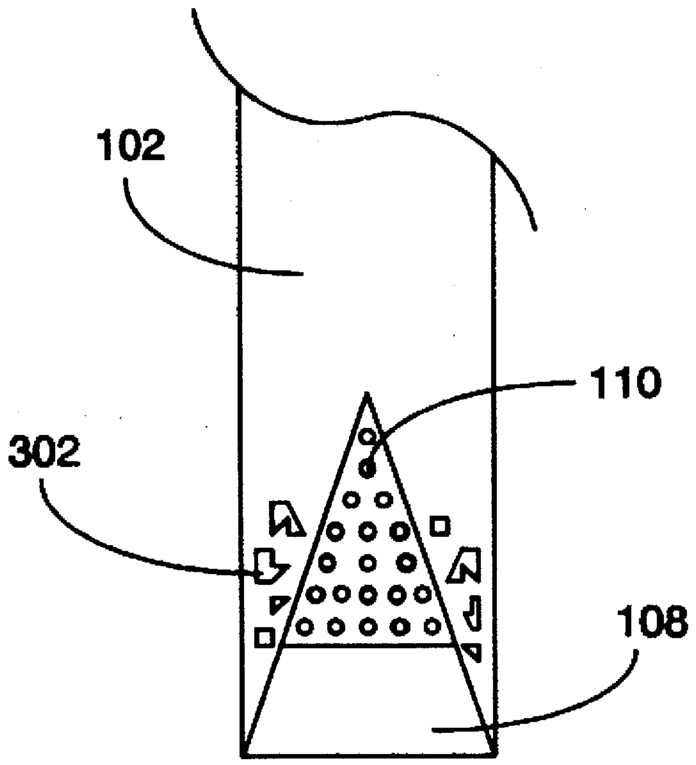
FIG. 3 illustrates the particle barrier used in the preferred embodiment.

FIG. 3 illustrates powdered medicine or crushed tablets (hereinafter medication 302) resting against particle barrier 108 after loading into straw 100. When straw 100 is used by the patient, fluid enters fluid tube 102 through barrier apertures 110 and dissolves medication 302 while it is being pulled up through the straw 100. FIG. 3 also illustrates the preferred embodiment of the particle barrier 108 which is cone shaped. A cone shape is preferred due to its simplicity of construction.

Figure 4:
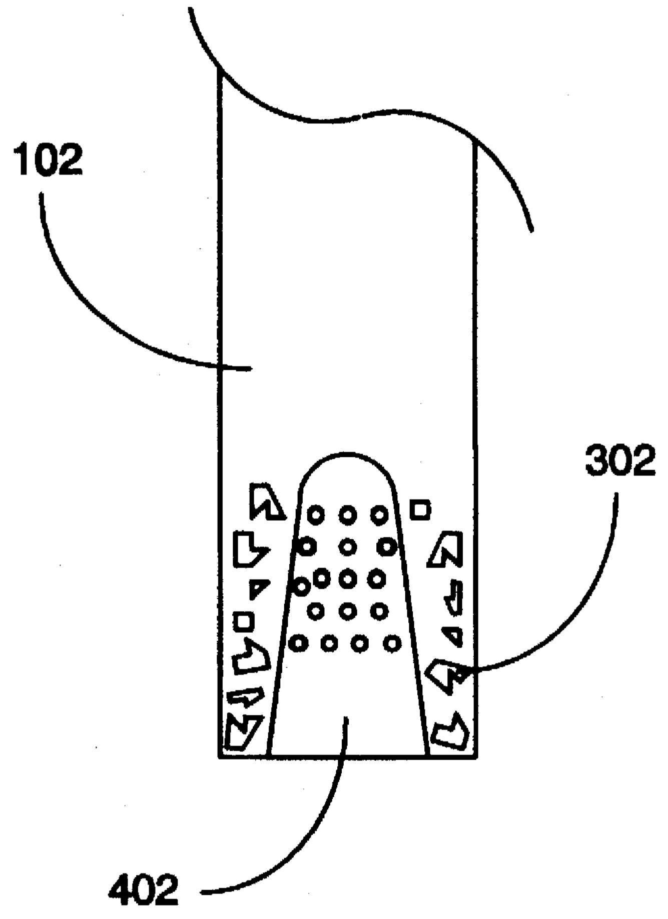
FIG. 4 illustrates an alternative embodiment of the particle barrier.

FIG. 4 illustrates an alternative embodiment for the particle barrier 108. In this embodiment, Particle barrier 108 has a rounded cone shape and provides more room for medication 302. Those skilled in the art will recognize that there are any number of shapes which can be used for the particle barrier 108 so long as they are able to be conveniently used with straw 100.

Figure 5:
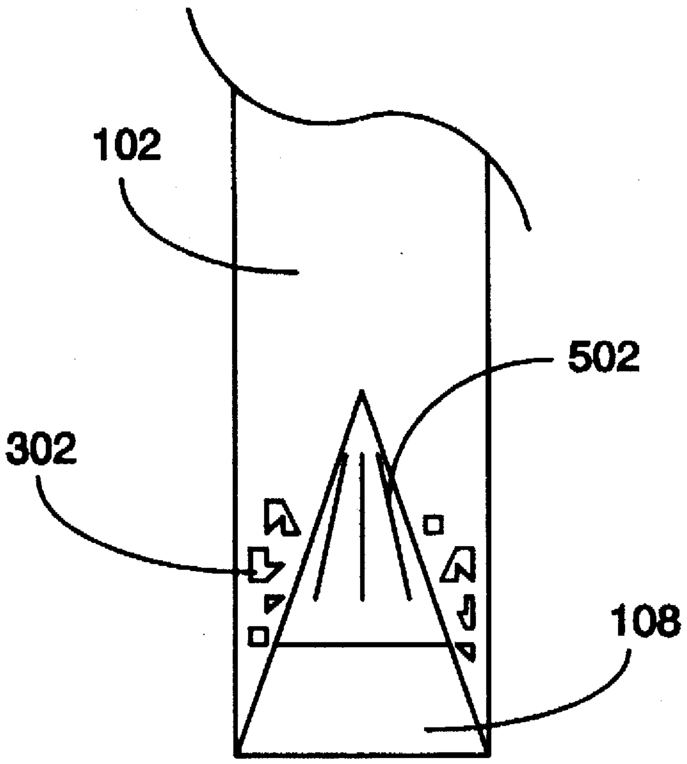
FIG. 5 illustrates another alternative embodiment of the particle barrier.

In FIG. 5, the preferred embodiment of particle barrier is shown which uses slits 502 instead of barrier apertures 110. The advantage of slits 502 over the previously discussed embodiments is that they are much simpler to manufacture. In addition, they form a tighter seal than barrier apertures 110 prior to use, which avoids any inadvertent discharge of medicine 302.

Figure 6:
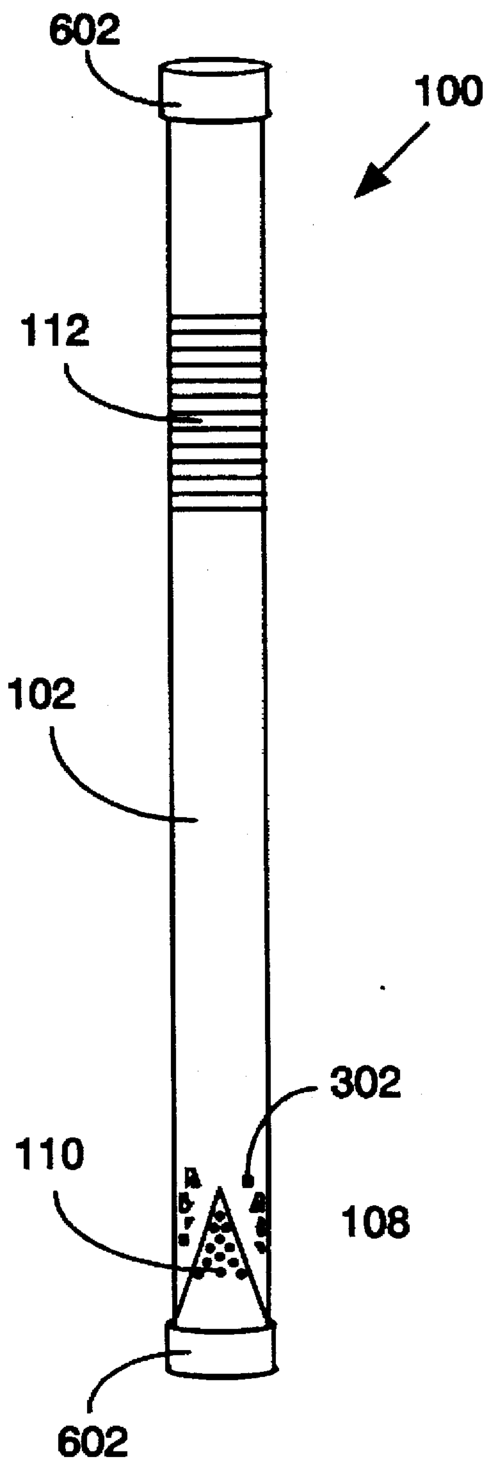
FIG. 6 is an alternative embodiment of the medication delivery straw preloaded with dry medicine and capped at both ends.

FIG. 6 illustrates another alternative embodiment similar to that shown above, in FIG. 1. However, in this embodiment, caps 602 are used to seal straw 100. Caps 602 allow medication 302 to be preloaded into straw 100 at its point of manufacture. For commonly used medicines, this embodiment saves the nurse additional time. When a patient needs to be medicated, the nurse merely removes caps 602 and gives straw 100 to the patient for use. Caps 602 can be secured to straw 100 in any convenient manner, such as pressure fit, screw-on, tape, adhesive, etc.

Figure 7:
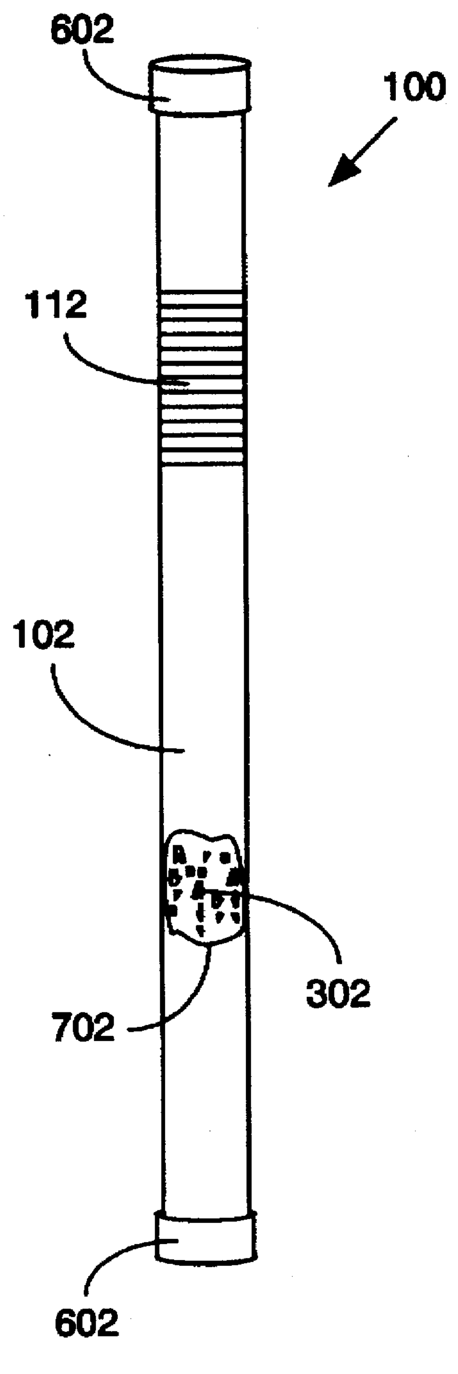
FIG. 7 is another alternative embodiment preloaded with dry medicine which is enclosed in a porous sack secured to the fluid path of the medication delivery straw.

FIG. 7 illustrates another preferred embodiment in which a preselected dosage of dry medication is shown as medication 302. The medication 302 is held in a porous sack 702. During manufacture, porous sack 702 is secured to the inside of straw 100 by any convenient means. In use, porous sack 702 and medication 302 function in a fashion similar to a common teabag. Since porous sack 702 is in the path of fluid flow, the medication 302 is dissolved by the fluid as it passes through straw 100 and is ingested by the patient.

Figure 8:
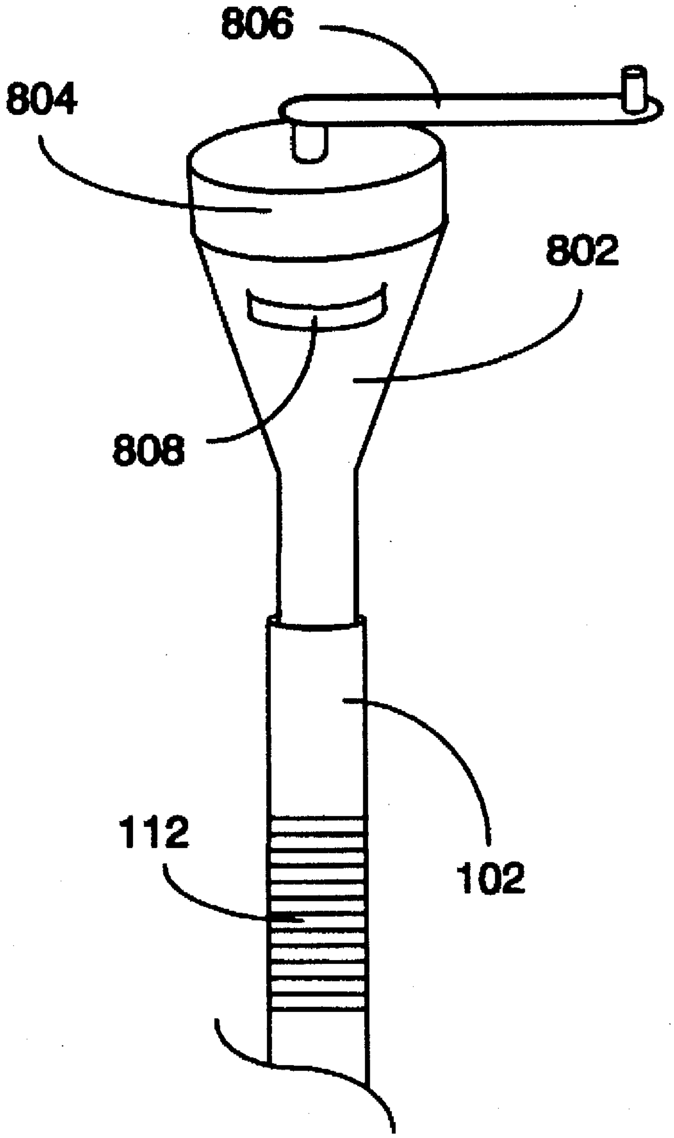
FIG. 8 is another alternative embodiment which uses a tablet grinder in conjunction with a reusable funnel.

FIG. 8 illustrates an alternative embodiment which employs a reusable funnel 802 in conjunction with a pill grinder 804. In this embodiment, each patient has an individual reusable funnel 802 which is identified by label 808. Reusable funnel 802 is attached to pill grinder 804 by any convenient method such as a threaded attachment, pressure fit, etc. Pill grinder 804 has a handle 806 which is turned to crush the tablet (not shown) held within pill grinder 804. Pill grinders 804 are well known in the art. This embodiment reduces cost by allowing a single pill grinder 804 to be used for multiple patients. In addition, the cost of reusable funnel 802 is reduced because each patient only requires a single reusable funnel 802.

Figure 9A:
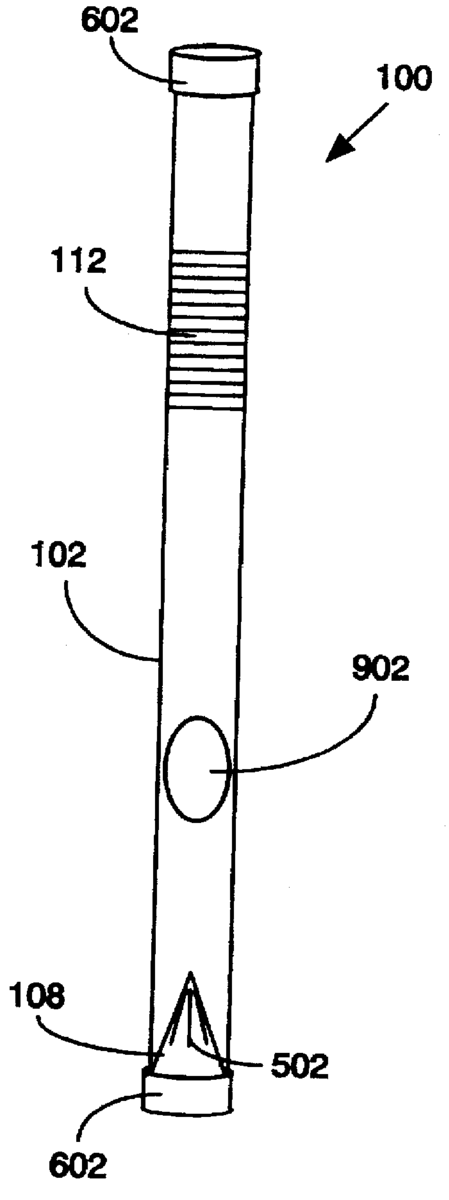
FIG. 9A is another alternative embodiment preloaded with a crushable medicine tablet which, prior to use, is manually crushed inside the fluid path of the medication delivery straw.

In FIG. 9A, another alternative preferred embodiment is shown. In this embodiment, a crushable tablet of medicine is stored within straw 100 prior to use. Fluid tube 102 is preferably made from a sturdy flexible material such as a flexible plastic. Before administering the medication, fluid tube 102 is squeezed to crush medicine tablet 902. This embodiment eliminates the need for a funnel and permits the nurse to rapidly and efficiently administer the medicine tablet 902 without ever coming in contact with it. Also shown in this embodiment are slits 502 (which are the preferred method of allowing fluid entrance into fluid tube 102) and caps 602. A principle advantage of this embodiment is that straw 100 is a completely self contained medicine container and delivery system which is resistant to contamination due to the fact that medicine 902 is never handled outside of straw 100.

Figure 9B:
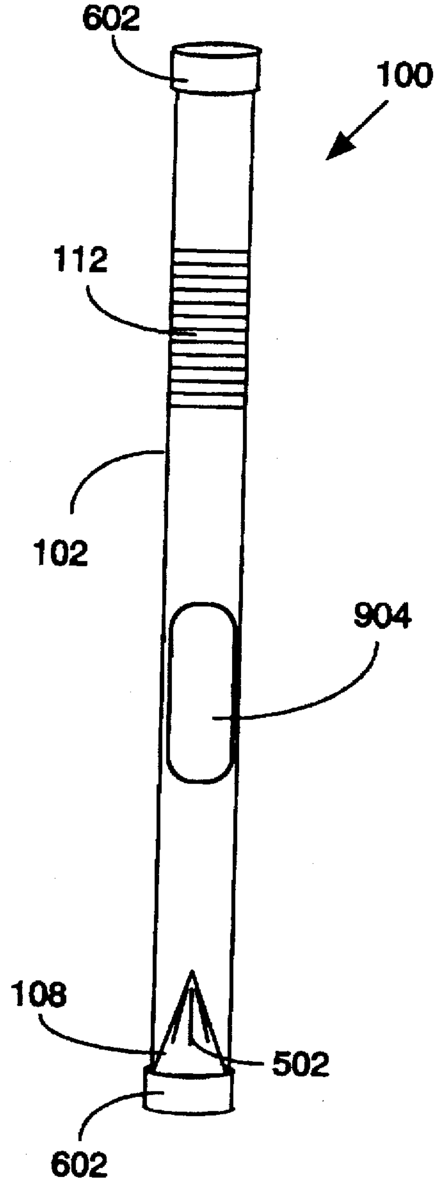
FIG. 9B is another alternative embodiment preloaded with a breakable cartridge which, prior to use, is manually broken to release medication inside the fluid path of the medication delivery straw.

Regarding FIG. 9B, the embodiment of FIG. 9B is similar to that shown above in FIG. 9A. However, this embodiment replaces the crushable tablet 902 with a breakable cartridge 904 that contains medicine 302. Fluid tube 102 is squeezed prior to use to cause breakable cartridge 904 to rupture. When ruptured, breakable cartridge 904 releases medicine 302 into the fluid path of straw 100. Once released, medicine 302 is absorbed by fluid passing through straw 100 and ingested by the patient.

Figure 10A:
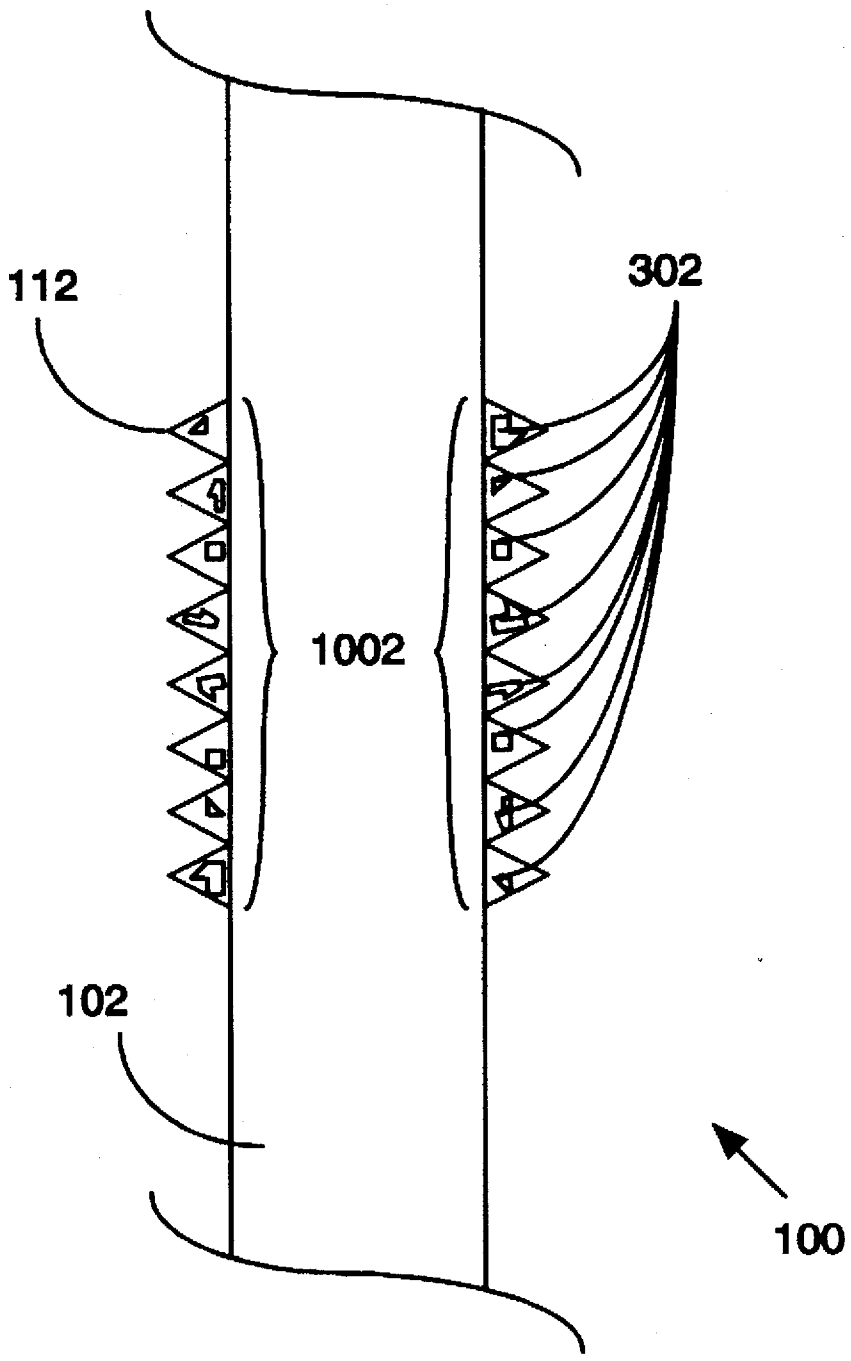
FIG. 10A illustrates a preferred embodiment of the medication delivery straw with medicine preloaded into the flexible neck.
Figure 10B:
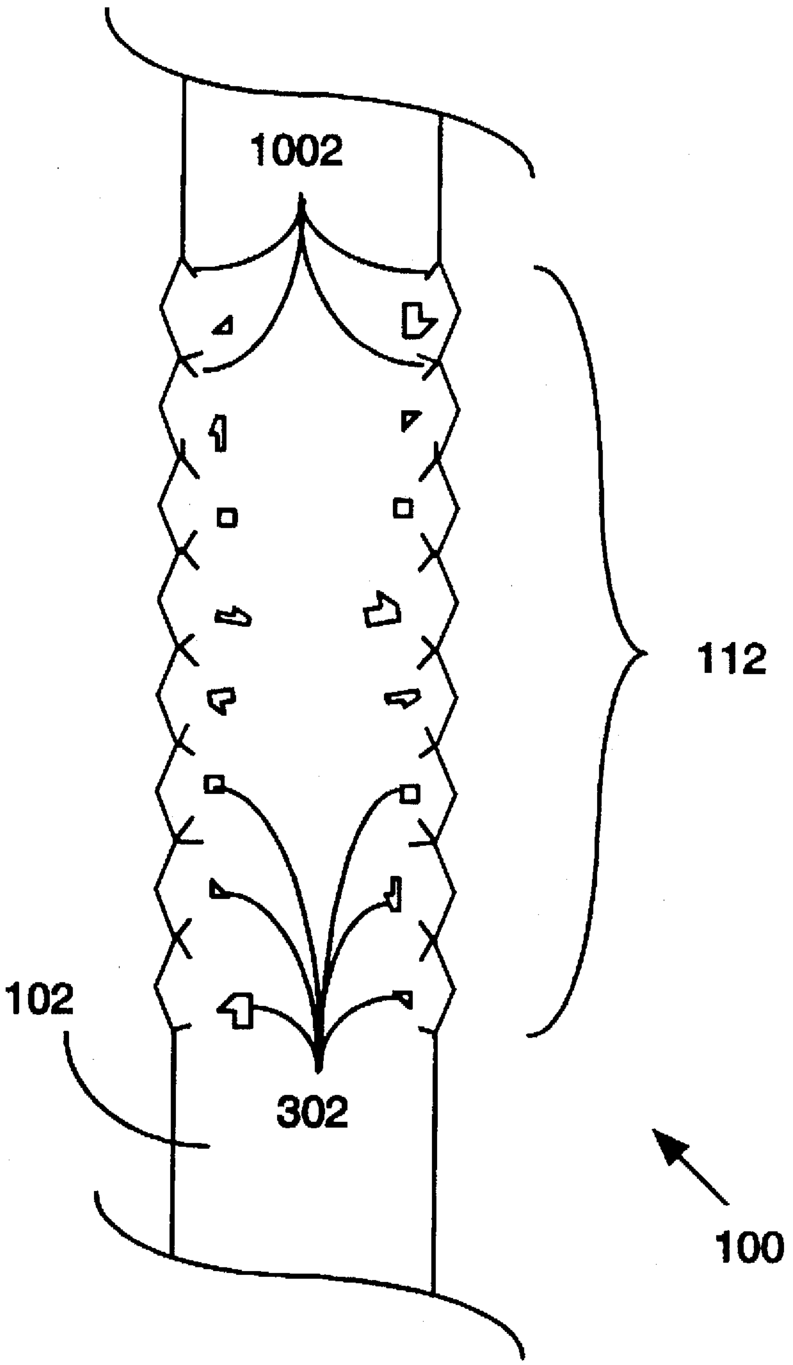
FIG. 10B shows the embodiment of FIG. 10A with the flexible neck extended prior to use and with the medicine released into the fluid tube.

FIGS. 10A–B illustrate another alternative embodiment which stores medicine 302 in flexible neck 112 prior to use. As shown in FIG. 10A, a thin breakable membrane 1002 holds medicine 302 inside of flexible neck 112 so long as flexible neck is not extended. The flexible neck 112 and breakable membrane 1002 form a medicine storage compartment (i.e., a pocket).

FIG. 10B illustrates the effect of extending flexible neck 112. When flexible neck 112 is extended, membrane 1002 is broken, and in turn, medicine 302 is released into the fluid path of straw 100. Membrane 1002 can be made from any suitable material, such as paper, plastic, polyethylene, etc. Any suitable method of attaching membrane 1002 to flexible neck 112 can be used (For example: adhesive) so long as the ripped segments of membrane 1002 are held securely to the inside of fluid tube 102 and are prevented from being ingested by the patient. However, those skilled in the art will recognize that a breakable membrane made from an edible (and perhaps dissolvable) material will avoid any potential problems associated with non-digestible materials. Edible materials which can be formed into a flat membrane-like layer are well known in the art. An advantage of this embodiment is that medicine 302 can be preloaded into straw 100 without the use of caps 602. As a result, the cost of straw 100 can be reduced.

Figure 11:
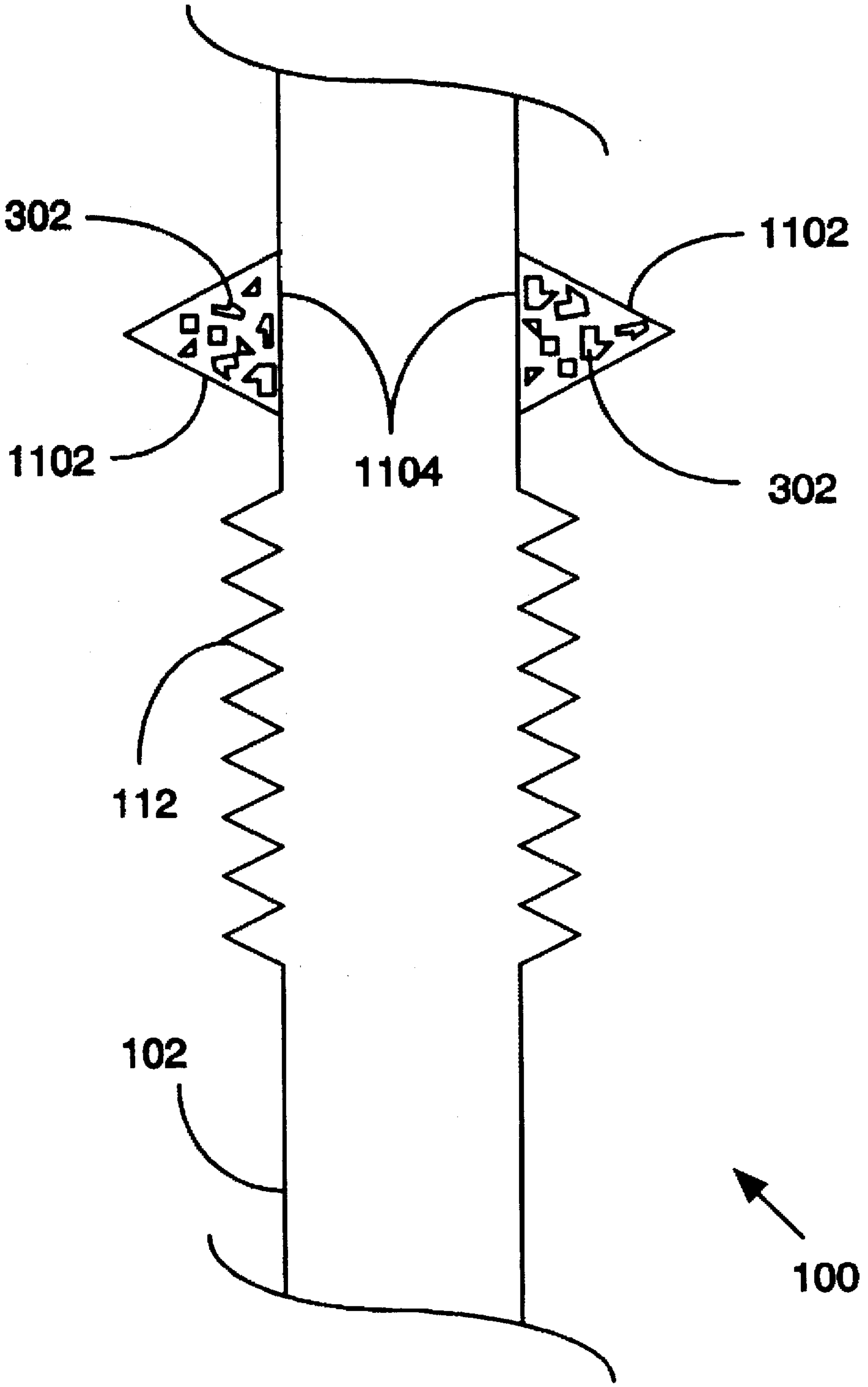
FIG. 11 shows an alternative embodiment with a self contained medicine storage compartment within the wall of the fluid tube.

FIG. 11 is an alternative embodiment similar to the embodiment shown in FIGS. 10A–B. In this embodiment, the flexible neck 112 is not used to store the preloaded dosage of medicine. In fact, optional flexible neck 112 is not required to implement this embodiment and is shown only to illustrate that it can be used in conjunction with extendable compartment 1102. A separate extendable compartment 1102 contains medicine 302. Similar to the embodiment of FIG. 10A–B, a breakable membrane 1104 retains medicine 302 within the pocket formed by extendable compartment 1102 and breakable membrane 1104 prior to use. When the medicine 302 is to be delivered, straw 100 is extended to break membrane 1102 and release medicine 302 into the fluid tube 102 in the same manner as medicine 302 was released in the previous embodiment.

Figure 12:
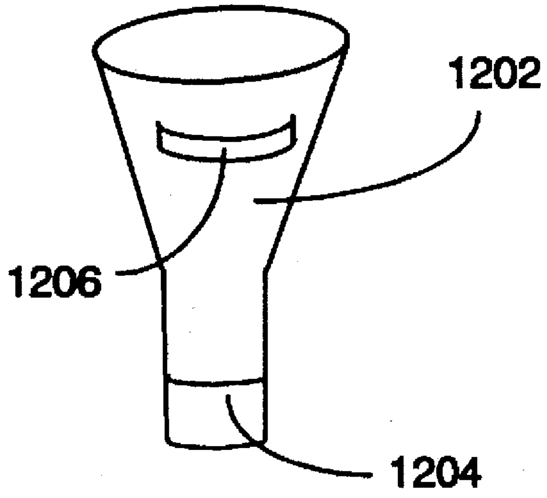
FIG. 12 shows an alternative funnel embodiment which uses a funnel that is preloaded with medicine.

In FIG. 12, an alternative funnel embodiment is shown. In this embodiment, funnel 1202 is preloaded with medicine 302. The specific type of medicine 302 is indicated on label 1206. A removable tip 1204 allows the nurse to select the necessary medication, remove tip 1204 and insert funnel 1202 into straw 100 to load the straw with medicine 302. The medicine 302 can be precrushed or can be in tablet form and crushed in funnel 1202 prior to the removal of tip 1204. While funnel 1202 is illustrated in FIG. 11 as having a traditional funnel shape, those skilled in the art will recognize that funnel 1202 can have any convenient shape so long as medicine 302 can be delivered to straw 100. Funnel 1202 is closed at the top rather than open as a conventional funnel is structured. This allows funnel 1202 to be inverted while removable tip 1204 is removed. It also provides a sealed chamber to safely store medicine 302 prior to use.

The foregoing discussion has referred to the use of the medicine delivery system, including straw 100, funnel 1202, etc. as being used by Medical Professionals such as doctors, nurses, etc. However, the system disclosed herein can be used by anyone who desires a convenient method of administering medication (i.e. the general public.)

Likewise, the foregoing discussion has used dry medicines for ease of illustration. However, those skilled in the arts will realize that non-dry medicines may also be used so long as they as viscous enough to prevent leakage through the particle barrier.

While the invention has been described with respect to a preferred embodiment thereof, it will be understood by those skilled in the art that various changes in detail may be made therein without departing from the spirit, scope, and teaching of the invention. For example, a variety of techniques can be used in addition to barrier apertures 110. A fine mesh can be secured to the end of fluid tube 110. Porous paper, such as that used for ordinary teabags, can also be substituted. Also, any material suitable for construction of an ordinary drinking straw can be used to construct fluid tube 102. Accordingly, the invention disclosed herein is to be limited only as specified in the following claims.

I claim:

1. A method of delivering medicine with a straw including the steps of:

drawing liquids into a fluid tube having a proximal end and a distal end, the proximal end having a proximal aperture to allow liquids to be drawn through the fluid tube under suction pressure, the proximal aperture sufficiently large enough to allow medicine to be inserted into the fluid tube at the proximal aperture;

inserting particles of medicine into the fluid tube; and retaining the particles of medicine in the fluid tube until they are dissolved by liquid entering the tube with a particle barrier at the distal end, the particle barrier having barrier apertures sufficiently large enough to allow liquid to enter the distal end, the barrier apertures sufficiently small enough to prevent substantially all of the particles of the medicine from passing through the particle barrier;

whereby the medicine is mixed with the liquid when the liquid is pulled through the fluid tube under suction pressure.

2. A method, as in claim 1, wherein the step of inserting the medicine is accomplished using a funnel, the, funnel having a spout, at least a portion of the spout having an outside diameter smaller than the inside diameter of the proximal aperture such that it can be inserted into the proximal aperture.

3. A method, as in claim 2, including the further step of using a flexible neck in the fluid tube.

4. A method, as in claim 1,including the further step of shaping the particle barrier such that it is substantially cone shaped having a distal end attached to the fluid tube and a proximal end extending into the fluid tube toward the proximal end of the fluid tube, the particle barrier further having at least one fluid aperture sufficiently large enough to allow liquid to flow into the fluid tube and sufficiently small enough to prevent substantially all of the medicine from passing through the particle barrier.

5. A method, as in claim 4,including the further step of locating substantially all of the fluid apertures in a portion of particle barrier near the proximal end of the particle barrier.

6. A method, as in claim 5, wherein the step of inserting the medicine is accomplished using a funnel, the funnel having a spout, at least a portion of the spout having an outside diameter smaller than the inside diameter of the proximal aperture such that it can be inserted into the proximal aperture.

7. A method, as in claim 4, including the further step of forming at least one of the fluid apertures in the form of a pinhole in the particle barrier.

8. A method, as in claim 7, wherein the step of inserting the medicine is accomplished using a funnel, the funnel having a spout, at least a portion of the spout having an outside diameter smaller than the inside diameter of the proximal aperture such that it can be inserted into the proximal aperture.

9. A method, as in claim 4, including the further step of forming at least one of the fluid apertures in the form of a slit in the particle barrier.

10. A method, as in claim 9, wherein the step of inserting the medicine is accomplished using a funnel, the funnel having a spout, at least a portion of the spout having an outside diameter smaller than the inside diameter of the proximal aperture such that it can be inserted into the proximal aperture.

11. A medicine delivery straw for use with medicine, comprising:

a fluid tube having a proximal end and a distal end, the proximal end having a proximal aperture to allow liquids to be drawn through the fluid tube under suction pressure, the proximal aperture sufficiently large enough to allow medicine to be inserted into the fluid tube at the proximal aperture: and a particle barrier at the distal end, the particle barrier having barrier apertures sufficiently large enough to allow liquid to enter the distal end, the barrier apertures sufficiently small enough to prevent substantially all of the particles of the medicine from passing through the particle barrier and to retain the particles in the fluid tube until they are dissolved by liquid entering the tube:

a funnel having a spout, at least a portion of the spout having an outside diameter smaller than the inside diameter of the proximal aperture such that it can be inserted into the proximal aperture, the funnel further having a removable tip on the end of the spout such that the funnel forms an enclosed medicine storage compartment prior to removal of the removable tip;

a preselected dosage of medicine;

whereby the medicine is mixed with the liquid when the liquid is pulled through the fluid tube under suction pressure and the medicine can be inserted into the fluid tube with the funnel.

12. A medicine delivery straw for use with medicine comprising:

a fluid tube having a proximal end and a distal end, the proximal end having a proximal aperture to allow liquids to be drawn through the fluid tube under suction pressure, the proximal aperture sufficiently large enough to allow medicine to be inserted into the fluid tube at the proximal aperture;

a particle barrier at the distal end, the particle barrier having barrier apertures sufficiently large enough to allow liquid to enter the distal end, the barrier apertures sufficiently small enough to prevent substantially all of the particles of the medicine from passing through the particle barrier;

a tablet crusher in medicine tablets; and a funnel having a spout, at least a portion of the spout having an outside diameter smaller than the inside diameter of the proximal aperture such that it can be inserted into the proximal aperture; the funnel further having means for attachment to the tablet crusher;

whereby crushed medicine tablets crushed by the tablet crusher can be inserted into the fluid tube with the funnel and the crushed medicine tablets are mixed with the liquid when the liquid is pulled through the fluid tube under suction pressure.

13. A medicine delivery straw for use with medicine, comprising:

a fluid tube having a proximal end and a distal end, the proximal end having a proximal aperture to allow liquids to be drawn through the fluid tube under suction pressure, the proximal aperture sufficiently large enough to allow medicine to be inserted into the fluid tube at the proximal aperture;

a particle barrier at the distal end, the particle barrier having barrier apertures sufficiently large enough to allow liquid to enter the distal end, the barrier apertures sufficiently small enough to prevent substantially all of the particles of the medicine from passing through the particle barrier;

the proximal end of the fluid tube forms a funnel portion; and the fluid tube further comprises a weakened point between the funnel portion and remainder of the fluid tube;

whereby the funnel can be detached from the fluid tube after the medicine is inserted into the fluid tube and the medicine are mixed with the liquid when the liquid is pulled through the fluid tube under suction pressure.

14. A medicine delivery straw, as in claim 13, wherein the fluid tube further comprises a flexible neck.

15. A medicine delivery system for use with a medicine, comprising:

a medicine sack, further comprising:

a preselected dosage of medicine; and a particle barrier, the particle barrier encapsulating the preselected dosage of medicine, the particle barrier further capable of allowing fluid to pass through the particle barrier and further capable of preventing the medicine from passing through the particle barrier until dissolved or suspended in fluid; and a straw, further comprising:

a fluid tube having a proximal end and a distal end, the proximal end having a proximal aperture to allow liquids to be drawn through the fluid tube under suction pressure, the fluid tube further having means to securely hold the medicine sack in the path of the fluid when the medicine sack is inserted into the fluid tube;

whereby the preselected dosage of medicine is mixed with the liquid when the liquid is pulled through the fluid tube under suction pressure.

16. A medicine delivery straw, as in claim 15, wherein:

the fluid tube further comprises a flexible neck.

17. A medicine delivery straw, comprising:

a preselected dosage of medicine;

a fluid tube having a proximal end and a distal end, the proximal end having a proximal aperture to allow liquids to be drawn through the fluid tube under suction pressure;

a particle barrier attached to the distal end of the fluid tube, the particle barrier having barrier apertures sufficiently large enough to allow fluid to enter the distal end, the barrier apertures sufficiently small enough to prevent substantially all of the preselected dosage of medicine from passing through the particle barrier; and a removable cap attached to the proximal end of the fluid tube to hold the preselected dosage of medicine in the fluid tube prior to use;

whereby the medicine is mixed with the liquid when the liquid is pulled through the fluid tube under suction pressure.

18. A medicine delivery straw, as in claim 17, wherein:

the fluid tube further comprises a flexible neck.

19. A medicine delivery straw, as in claim 18, wherein:

the preselected dosage of medicine is a crushable tablet; and the fluid tube is sufficiently flexible to allow the crushable tablet to be crushed inside the fluid tube prior to use.

20. A medicine delivery straw, as in claim 18, wherein:

the preselected dosage of medicine is contained in a breakable cartridge; and the fluid tube is sufficiently flexible to allow the breakable cartridge to be ruptured inside the fluid tube prior to use;

whereby medicine is released from the breakable cartridge.

21. A medicine delivery straw, as in claim 18, wherein:

a breakable membrane is secured to the inside of the fluid tube, the breakable membrane attached to the inside of the flexible neck such that each fold in the flexible neck forms an enclosed pocket;

the preselected dosage of medicine is stored within the pockets formed by the breakable membrane and the folds of the flexible neck; and the flexible neck, when extended, is longer than the length of the membrane and causes the membrane to rupture and release the medicine into the fluid tube.

22. A medicine delivery straw, as in claim 18, wherein:

at least one extendable compartment formed on the side of the flexible neck;

a breakable membrane is secured to the inside of an extendable compartment such that the extendable compartment forms an enclosed pocket;

the preselected dosage of medicine is stored within the pocket formed by the breakable membrane and the extendable compartment; and the extendable compartment, when extended, is longer than the length of the membrane and causes the membrane to rupture and release the medicine into the fluid tube.

23. A medicine delivery straw, as in claim 17, wherein:

the particle barrier is substantially cone shaped having a distal end attached to the fluid tube and a proximal end extending into the fluid tube toward the proximal end of the fluid tube, the particle barrier further having at least one fluid aperture sufficiently large enough to allow fluid flow into the fluid tube and sufficiently small enough to prevent substantially all of the preselected dosage of medicine from passing through the particle barrier.

24. A medicine delivery straw, as in claim 23, wherein:

the fluid tube further comprises a flexible neck.

* * * * *